(12) United States Patent
Errico et al.

(10) Patent No.: US 11,298,156 B2
(45) Date of Patent: Apr. 12, 2022

(54) MODULAR SCREW

(71) Applicant: K2M, Inc., Leesburg, VA (US)

(72) Inventors: Thomas J. Errico, New York, NY (US); Peter Newton, La Jolla, CA (US); Harry Shufflebarger, Jupiter, FL (US); Larry E. McClintock, Gore, VA (US)

(73) Assignee: K2M, Inc., Leesburg, VA (US)

( * ) Notice: Subject to any disclaimer, the term of this patent is extended or adjusted under 35 U.S.C. 154(b) by 70 days.

(21) Appl. No.: 16/498,812

(22) PCT Filed: Mar. 28, 2018

(86) PCT No.: PCT/US2018/024832
§ 371 (c)(1),
(2) Date: Sep. 27, 2019

(87) PCT Pub. No.: WO2018/183489
PCT Pub. Date: Oct. 4, 2018

(65) Prior Publication Data
US 2020/0030006 A1 Jan. 30, 2020

Related U.S. Application Data

(60) Provisional application No. 62/478,691, filed on Mar. 30, 2017.

(51) Int. Cl.
*A61B 17/70* (2006.01)
*A61B 17/86* (2006.01)

(52) U.S. Cl.
CPC ...... *A61B 17/7035* (2013.01); *A61B 17/7037* (2013.01); *A61B 17/8685* (2013.01)

(58) Field of Classification Search
CPC .............. A61B 17/7032–7037; A61B 17/8685
See application file for complete search history.

(56) References Cited

U.S. PATENT DOCUMENTS

| | | | |
|---|---|---|---|
| 5,382,248 A | 1/1995 | Jacobson et al. |
| 5,487,744 A | 1/1996 | Howland |
| 5,725,528 A | 3/1998 | Errico et al. |
| 5,735,851 A | 4/1998 | Errico et al. |

(Continued)

OTHER PUBLICATIONS

International Search Report from Application No. PCT/US2018/024832 dated Jun. 8, 2018, pp. 1-2.

*Primary Examiner* — Julianna N Harvey
(74) *Attorney, Agent, or Firm* — Lerner, David, Littenberg, Krumholz & Mentlik, LLP

(57) ABSTRACT

A modular screw includes a post and a head assembly. The post includes a tapered portion extending along a length of the post, the post defining a first bore. The head assembly is adjustably coupled with the post. The head assembly includes a head defining a slot configured to receive a spinal rod therein, an elongate screw having external threads extending along a length of the elongate screw, and a screw shank defining a second bore configured to receive the elongate screw therein. The screw shank includes an engaging portion configured to expand radially outward when the elongate screw engages the engaging portion, and internal threads configured to engage the external threads of the elongate screw. At least a portion of the screw shank is dimensioned to be selectively received in the first bore of the post.

17 Claims, 6 Drawing Sheets

(56) References Cited

U.S. PATENT DOCUMENTS

| | | |
|---|---|---|
| 5,800,435 A | 9/1998 | Errico et al. |
| 6,004,322 A | 12/1999 | Bernstein |
| 6,050,997 A | 4/2000 | Mullane |
| 6,146,383 A | 11/2000 | Studer et al. |
| 6,482,207 B1 | 11/2002 | Errico |
| 6,623,485 B2 | 9/2003 | Doubler et al. |
| 6,669,697 B1 | 12/2003 | Pisharodi |
| 6,887,242 B2 | 5/2005 | Doubler et al. |
| 7,186,255 B2 | 3/2007 | Baynham et al. |
| 7,314,467 B2 | 1/2008 | Howland |
| 7,722,645 B2 | 5/2010 | Bryan |
| 7,766,943 B1 | 8/2010 | Fallin et al. |
| 8,007,518 B2 | 8/2011 | Winslow et al. |
| 8,012,181 B2 | 9/2011 | Winslow et al. |
| 8,016,861 B2 | 9/2011 | Mitchell et al. |
| 8,048,115 B2 | 11/2011 | Winslow et al. |
| 8,048,126 B2 | 11/2011 | Altarac et al. |
| 8,057,515 B2 | 11/2011 | Flynn et al. |
| 8,075,603 B2 | 12/2011 | Hammill, Sr. et al. |
| 8,083,772 B2 | 12/2011 | Winslow et al. |
| 8,083,775 B2 | 12/2011 | Winslow et al. |
| 8,083,777 B2 | 12/2011 | Butters et al. |
| 8,092,501 B2 | 1/2012 | Mitchell et al. |
| 8,097,024 B2 | 1/2012 | Winslow et al. |
| 8,114,134 B2 | 2/2012 | Winslow et al. |
| 8,137,384 B2 | 3/2012 | Heiges et al. |
| 8,192,468 B2 | 6/2012 | Biedermann et al. |
| 8,192,470 B2 | 6/2012 | Biedermann et al. |
| 8,197,518 B2 | 6/2012 | Hammill, Sr. et al. |
| 8,211,155 B2 | 7/2012 | Winslow et al. |
| 8,257,397 B2 | 9/2012 | Winslow et al. |
| 8,333,792 B2 | 12/2012 | Winslow et al. |
| 8,337,530 B2 | 12/2012 | Hestad et al. |
| 8,337,536 B2 | 12/2012 | Mitchell et al. |
| 8,430,916 B1 | 4/2013 | Winslow et al. |
| 8,506,609 B2 | 8/2013 | Biedermann et al. |
| 8,518,085 B2 | 8/2013 | Winslow et al. |
| 8,636,781 B2 | 1/2014 | Biedermann et al. |
| 8,636,782 B2 | 1/2014 | Biedermann et al. |
| 8,663,290 B2 | 3/2014 | Doubler et al. |
| 8,663,291 B2 | 3/2014 | Doubler et al. |
| 8,881,358 B2 | 11/2014 | Biedermann et al. |
| 8,900,270 B2 | 12/2014 | Fauth et al. |
| 8,926,671 B2 | 1/2015 | Biedermann et al. |
| 8,961,568 B2 | 2/2015 | McKinley et al. |
| 8,979,904 B2 | 3/2015 | Jackson et al. |
| 8,986,349 B1 | 3/2015 | German et al. |
| 8,992,579 B1 | 3/2015 | Gustine et al. |
| 8,998,958 B2 | 4/2015 | Dauster et al. |
| 9,017,390 B2 | 4/2015 | Biedermann et al. |
| 9,044,273 B2 | 6/2015 | Richelsoph et al. |
| 9,060,814 B2 | 6/2015 | Doubler et al. |
| 9,066,759 B2 | 6/2015 | Biedermann et al. |
| 9,119,674 B2 | 9/2015 | Matthis et al. |
| 9,131,971 B2 | 9/2015 | Biedermann et al. |
| 9,173,684 B2 | 11/2015 | Biedermann et al. |
| 9,186,187 B2 | 11/2015 | Mishra |
| 9,198,694 B2 | 12/2015 | Mishra et al. |
| 9,247,965 B2 | 2/2016 | Biedermann et al. |
| 9,254,150 B2 | 2/2016 | Biedermann et al. |
| 9,277,938 B2 | 3/2016 | Biedermann et al. |
| 9,277,941 B2 | 3/2016 | Biedermann et al. |
| 9,277,942 B2 | 3/2016 | Biedermann et al. |
| 9,333,016 B2 | 5/2016 | Biedermann et al. |
| 9,339,304 B2 | 5/2016 | Biedermann et al. |
| 9,358,047 B2 | 6/2016 | Mishra et al. |
| 9,364,266 B2 | 6/2016 | Biedermann et al. |
| 9,439,680 B2 | 9/2016 | Biedermann et al. |
| 9,451,990 B2 | 9/2016 | Fauth et al. |
| 9,452,006 B2 | 9/2016 | Biedermann et al. |
| 9,486,246 B2 | 11/2016 | Biedermann et al. |
| 9,492,204 B2 | 11/2016 | Biedermann et al. |
| 9,579,125 B2 | 2/2017 | Raju et al. |
| 9,603,635 B2 | 3/2017 | Leff et al. |
| 9,615,858 B2 | 4/2017 | Doubler et al. |
| 9,649,142 B2 | 5/2017 | Doubler et al. |
| 9,693,808 B2 | 7/2017 | Fauth et al. |
| 9,707,013 B2 | 7/2017 | Rezach et al. |
| 9,770,277 B2 * | 9/2017 | Biedermann ........ A61B 17/8685 |
| 9,820,780 B2 | 11/2017 | Duncan et al. |
| 9,883,892 B2 | 2/2018 | Jackson et al. |
| 9,895,170 B2 | 2/2018 | Biedermann et al. |
| 9,895,171 B2 | 2/2018 | Webb |
| 9,907,574 B2 | 3/2018 | Jackson et al. |
| 9,918,745 B2 | 3/2018 | Jackson et al. |
| 9,936,983 B2 | 4/2018 | Mesiwala et al. |
| 9,980,753 B2 | 5/2018 | Jackson et al. |
| 10,682,169 B2 * | 6/2020 | Biedermann ........ A61B 17/864 |
| 10,758,285 B2 * | 9/2020 | Geist ................ A61B 17/7035 |
| 11,129,657 B2 * | 9/2021 | Geist ................ A61B 17/7032 |
| 2002/0123752 A1 * | 9/2002 | Schultheiss .......... A61B 17/864 606/304 |
| 2003/0060823 A1 | 3/2003 | Bryan |
| 2008/0015596 A1 | 1/2008 | Whipple |
| 2009/0105771 A1 * | 4/2009 | Lei .................... A61B 17/7037 606/313 |
| 2010/0004692 A1 * | 1/2010 | Biedermann ...... A61B 17/7098 606/305 |
| 2010/0057135 A1 | 3/2010 | Heiges et al. |
| 2011/0118783 A1 | 5/2011 | Winslow et al. |
| 2011/0190830 A1 * | 8/2011 | Biedermann ...... A61B 17/8685 606/305 |
| 2011/0307018 A1 | 12/2011 | Zucherman et al. |
| 2012/0041490 A1 | 2/2012 | Jacob et al. |
| 2013/0338715 A1 | 12/2013 | Daly et al. |
| 2015/0196338 A1 | 7/2015 | Biedermann et al. |
| 2016/0030086 A1 | 2/2016 | Mishra |
| 2016/0030090 A1 | 2/2016 | Webb |
| 2016/0081719 A1 * | 3/2016 | Faulhaber .......... A61B 17/7032 606/309 |
| 2016/0220277 A1 | 8/2016 | Rezach et al. |
| 2016/0270826 A1 * | 9/2016 | Marino ............... A61B 17/844 |
| 2016/0278815 A1 * | 9/2016 | Fitzpatrick ......... A61F 2/30942 |
| 2017/0020574 A1 | 1/2017 | Biedermann et al. |
| 2017/0049482 A1 | 2/2017 | Campbell et al. |
| 2017/0049484 A1 | 2/2017 | Leff et al. |
| 2017/0065306 A1 | 3/2017 | Fauth et al. |
| 2017/0112542 A1 | 4/2017 | Biedermann et al. |
| 2017/0172630 A1 | 6/2017 | Biedermann et al. |
| 2017/0224386 A1 | 8/2017 | Leff et al. |
| 2017/0245898 A1 | 8/2017 | May et al. |
| 2017/0333085 A1 | 11/2017 | Jackson et al. |
| 2018/0014858 A1 | 1/2018 | Biester et al. |
| 2018/0014862 A1 | 1/2018 | Raina et al. |
| 2018/0014863 A1 | 1/2018 | Biester et al. |
| 2018/0036039 A1 | 2/2018 | Biedermann et al. |
| 2018/0055545 A1 | 3/2018 | Biedermann et al. |
| 2018/0070999 A1 * | 3/2018 | Biedermann ...... A61B 17/8685 |
| 2018/0092679 A1 | 4/2018 | Toon et al. |
| 2018/0110548 A1 | 4/2018 | May et al. |
| 2019/0159820 A1 * | 5/2019 | Geist ................ A61B 17/7037 |
| 2020/0146725 A1 * | 5/2020 | Geist ................ A61B 17/7035 |

* cited by examiner

MODULAR SCREW

CROSS-REFERENCE TO RELATED APPLICATIONS

The present application is a national phase entry under 35 U.S.C. § 371 of International Application No. PCT/US2018/024832, filed on Mar. 28, 2018, which claims priority to, and the benefit of, U.S. Provisional Patent Application Ser. No. 62/478,691, filed Mar. 30, 2017, the entireties of which are hereby incorporated by reference.

BACKGROUND

Technical Field

The present disclosure relates to a device for spinal surgery and, more particularly, to a modular screw.

Background of Related Art

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. It is common practice to place bone screws into vertebral bodies and then connect a metal rod to the bone screws, thus creating a rigid structure between adjacent vertebral bodies. In some cases, the use of these devices may be permanently implanted in the patient. In other cases, the devices may be implanted only as a temporary means of stabilizing or fixing the bones or bone fragments, with subsequent removal when no longer needed.

When using screws, the surgeon directs the screw into the vertebral body. Because different patients have different anatomies, screws may be inserted at different angles and at different heights relative to the operating field.

Fixation members that could reduce the time and labor required by a user to insert the fixation member, such as a screw, into a vertebra, while also providing the ability to adjust the height of the fixation member to ensure proper placement of mechanical hardware, such as rods and bands are desirable.

SUMMARY

The present disclosure describes a modular screw that demonstrates a practical approach to meeting the performance requirements and overcoming usability challenges associated with spinal surgeries. In accordance with an embodiment of the present disclosure, a modular screw includes a post and a head assembly. The post includes a tapered portion extending along a portion of a length of the post, the post defining a first bore. The head assembly is adjustably coupled with the post. The head assembly includes a head defining a slot configured to receive a spinal rod therein, an elongate screw having external threads extending along a portion of a length of the elongate screw, and a screw shank defining a second bore configured to receive the elongate screw therein. The screw shank includes an engaging portion configured to expand radially outward when the elongate screw engages the engaging portion, and internal threads configured to engage the external threads of the elongate screw. At least a portion of the screw shank is dimensioned to be selectively received in the first bore of the post.

In an embodiment, the engaging portion of the screw shank may define slits to facilitate radial expansion of the engaging portion.

In another embodiment, the engaging portion of the screw shank may include a gripping surface.

In yet another embodiment, a quarter of the engaging portion may have the gripping surface.

In still yet another embodiment, the gripping surface may include at least one of shallow threads, raised concentric rings, or a roughened surface.

In still yet another embodiment, the first bore of the post and the screw shank may have complementary cross-sections.

In an embodiment, the screw shank may include a polyaxial head and a shaft extending distally from the polyaxial head.

In another embodiment, the polyaxial head of the screw shank may be operatively coupled with the head for polyaxial movement relative to the head.

In yet another embodiment, the polyaxial head may include a bulbous shape.

In still yet another embodiment, the shaft of the screw shank may include a keyed outer surface.

In still yet another embodiment, the tapered portion of the post may extend at least a quarter of a length of the post. Alternatively, the tapered portion of the post may extend at least a half of a length of the post.

In an embodiment, the tapered portion of the post may include external threads.

In another embodiment, a major diameter of the tapered portion of the post may be in the range of about 10 mm and about 12 mm.

In yet another embodiment, the external threads of the elongate screw of the head assembly may extend at least a sixteenth of a length of the elongate screw. Alternatively, the external threads of the elongate screw of the head assembly may extend an eighth of a length of the elongate screw.

In still yet another embodiment, the external threads of the elongate screw of the head assembly may extend at least a quarter of a length of the elongate screw.

In still yet another embodiment, the elongate screw may define a cavity having a key feature for engagement with a driver to drive the elongate screw.

BRIEF DESCRIPTION OF THE DRAWINGS

Various embodiments of the present disclosure are described hereinbelow with reference to the drawings, wherein.

DETAILED DESCRIPTION

Figures 1, 2:
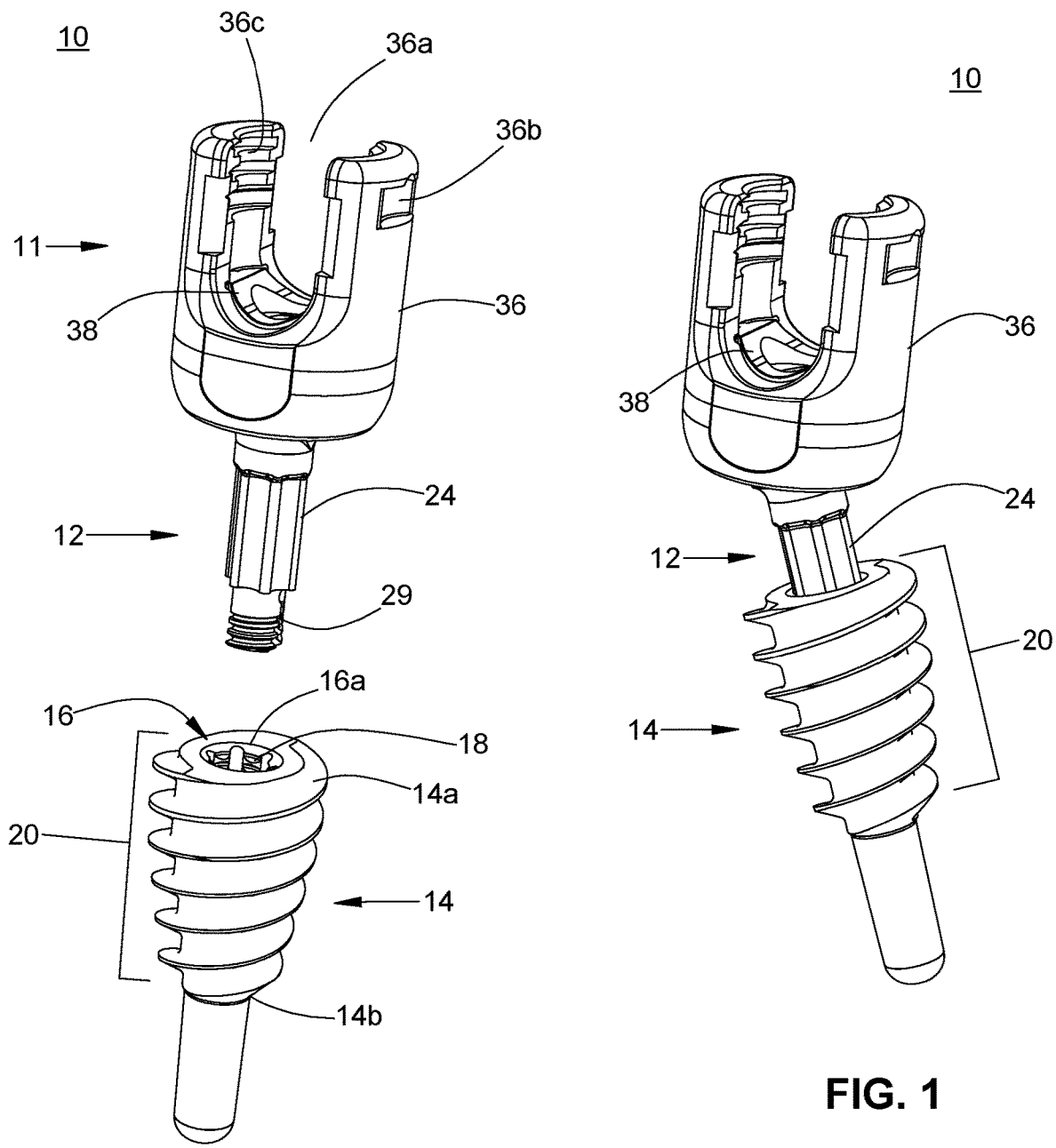
FIG. 1 is a perspective view of a modular screw in accordance with an embodiment of the present disclosure.
FIG. 2 is a perspective view of the modular screw of FIG. 1 with a housing assembly and a post separated.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In addition, the term "cephalad" is used in this application to indicate a direction toward a patient's head, while the term "caudad" indicates a direction toward the patient's feet. Further still, for the purposes of this application, the term "medial" indicates a direction toward the middle of the body of the patient, while the term "lateral" indicates a direction toward a side of the body of the patient, i.e., away from the middle of the body of the patient. The term "posterior" indicates a direction toward the patient's back, while the term "anterior" indicates a direction toward the patient's front. In the following description, well-known functions or constructions are not described in detail to avoid obscuring the present disclosure in unnecessary detail.

Figure 3:
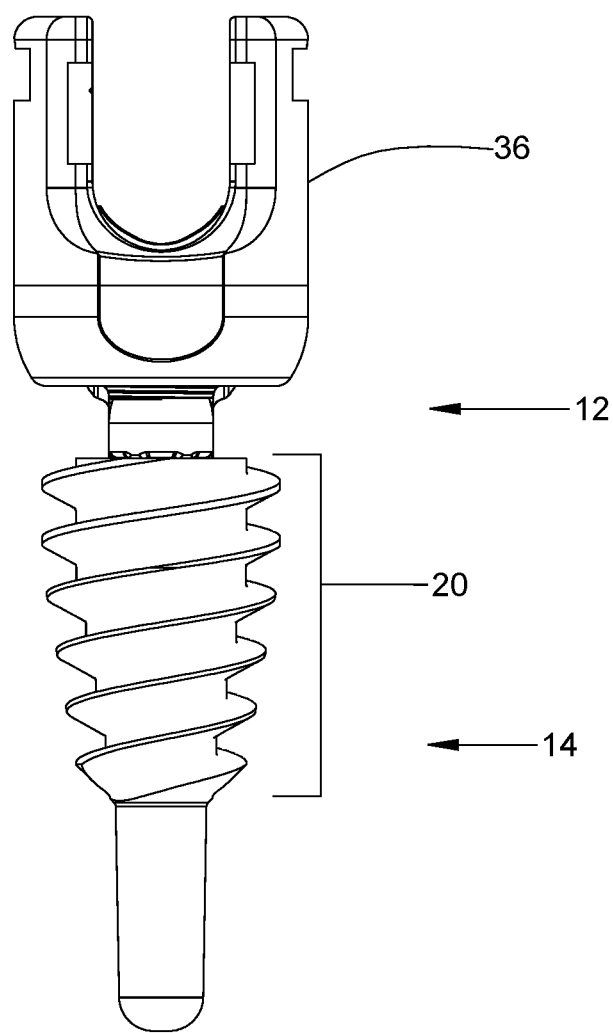
FIG. 3 is a side view of the modular screw of FIG. 1.

With reference to FIGS. 1-3, the present disclosure is directed to a modular polyaxial screw or modular screw 10 that is configured and adapted for use in a spinal surgical procedure. The modular screw 10 includes a post 14 and a head assembly 11 adjustably coupled to the post 14. The modular screw 10 provides the ability to selectively adjust the angle and the height of the head assembly 11 relative to the post 14 to ensure, e.g., proper placement of spinal rods and bands. With momentary reference to FIG. 7, the head assembly 11 includes a head 36, an anvil 38, an elongated screw 40, a screw shank 12, and a cap 42. Briefly, the modular screw 10 allows the head 36 to rotate and/or pivot with respect to the post 14 and also to be placed at one of several heights with respect to the post 14 providing additional flexibility in assembling a rod construct for a patient.

Referring now to FIG. 3, the head 36 can be configured and dimensioned to receive mechanical hardware (not shown) such as, e.g., a spinal rod or a band. The head 36 defines a slot 36a configured to receive, e.g., the spinal rod or the band (not shown). The slot 36a may include an arcuate profile to facilitate securement of the spinal rod therein. The head portion 36 includes inner walls 36c having threads configured to threadably receive a set screw (not shown) to secure the spinal rod in the slot 36a. The inner walls 36c may further define recesses or notches 36b configured to engage an instrument (e.g., a rod reducer). Reference may be made to U.S. Pat. Nos. 8,814,919 and 9,393,049, the entire contents of each of which are incorporated herein by reference, for a detailed description of the construction and operation of taper lock or set screw housing systems.

Figure 7:
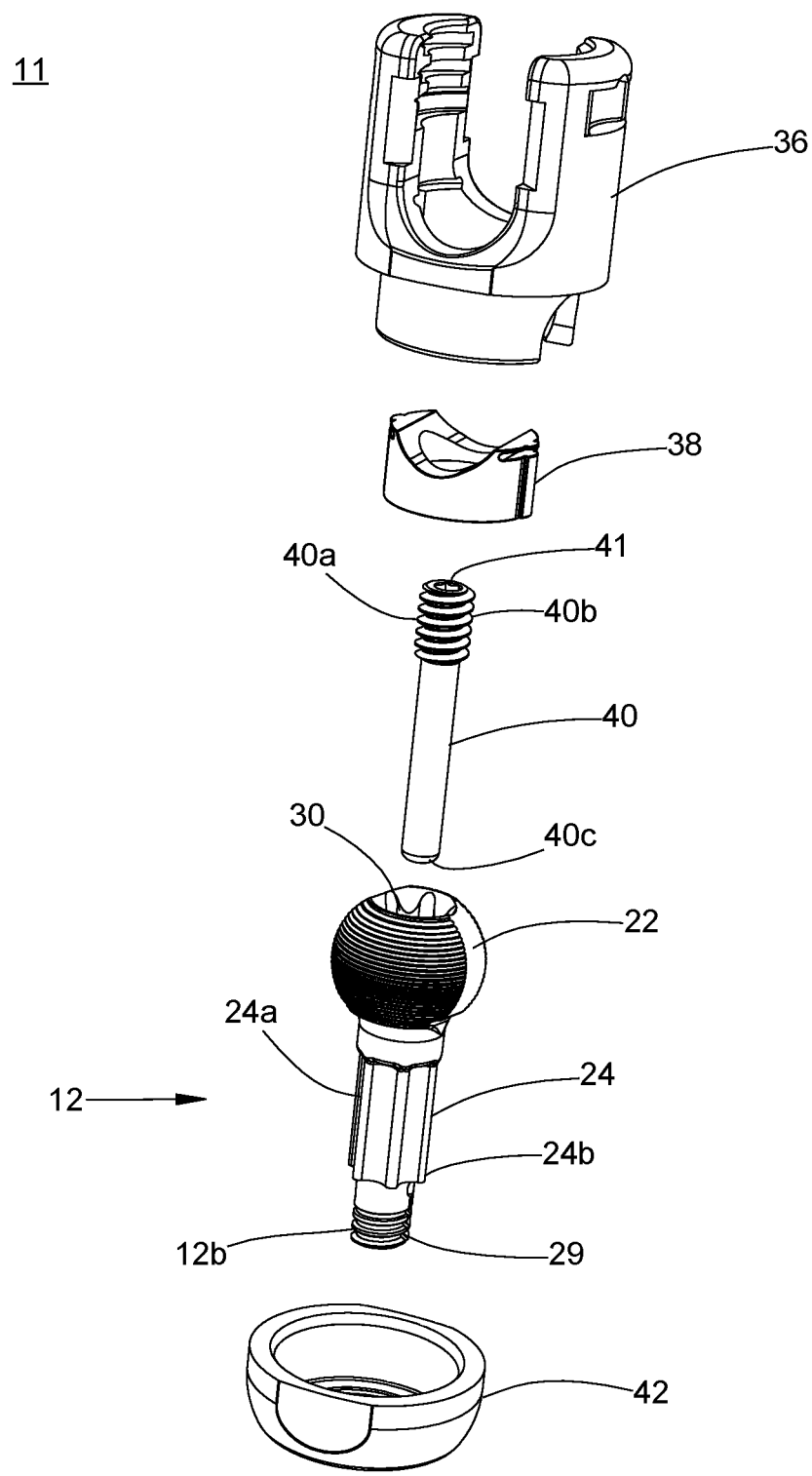
FIG. 7 is an exploded perspective view of the housing assembly of FIG. 2 with parts separated.

With additional reference to FIG. 7, the anvil 38 is configured to receive the elongate screw 40 and a portion of a head 22 of the screw shank 12. The elongate screw 40 includes helical threads 40a on an outer surface. The helical threads 40a extend from a proximal end 40b of the elongate screw 40 towards a distal end 40c of the elongate screw 40. For example, the helical threads 40a may extend at least a sixteenth of a length of the elongate screw 40. Alternatively, the helical threads 40a may extend at least an eighth of the length of the elongate screw 40. Furthermore, the helical threads 40 may extend, e.g., at least a quarter of a length, of the elongate screw 40. The helical threads 40a on the elongate screw 40 are configured to engage internal threads 12a (FIG. 10) of the screw shank 12.

The elongate screw 40 defines a cavity 41 at the proximal end 40b. The cavity 41 has, e.g., a hex, key feature for non-slip engagement with a driver or other instrument (not shown) to drive the elongate screw 40. It is contemplated that the cavity 41 may have any suitable configuration such as, e.g., slotted, square, star, or a Phillips head, for engagement with the driver.

Figures 9, 10:
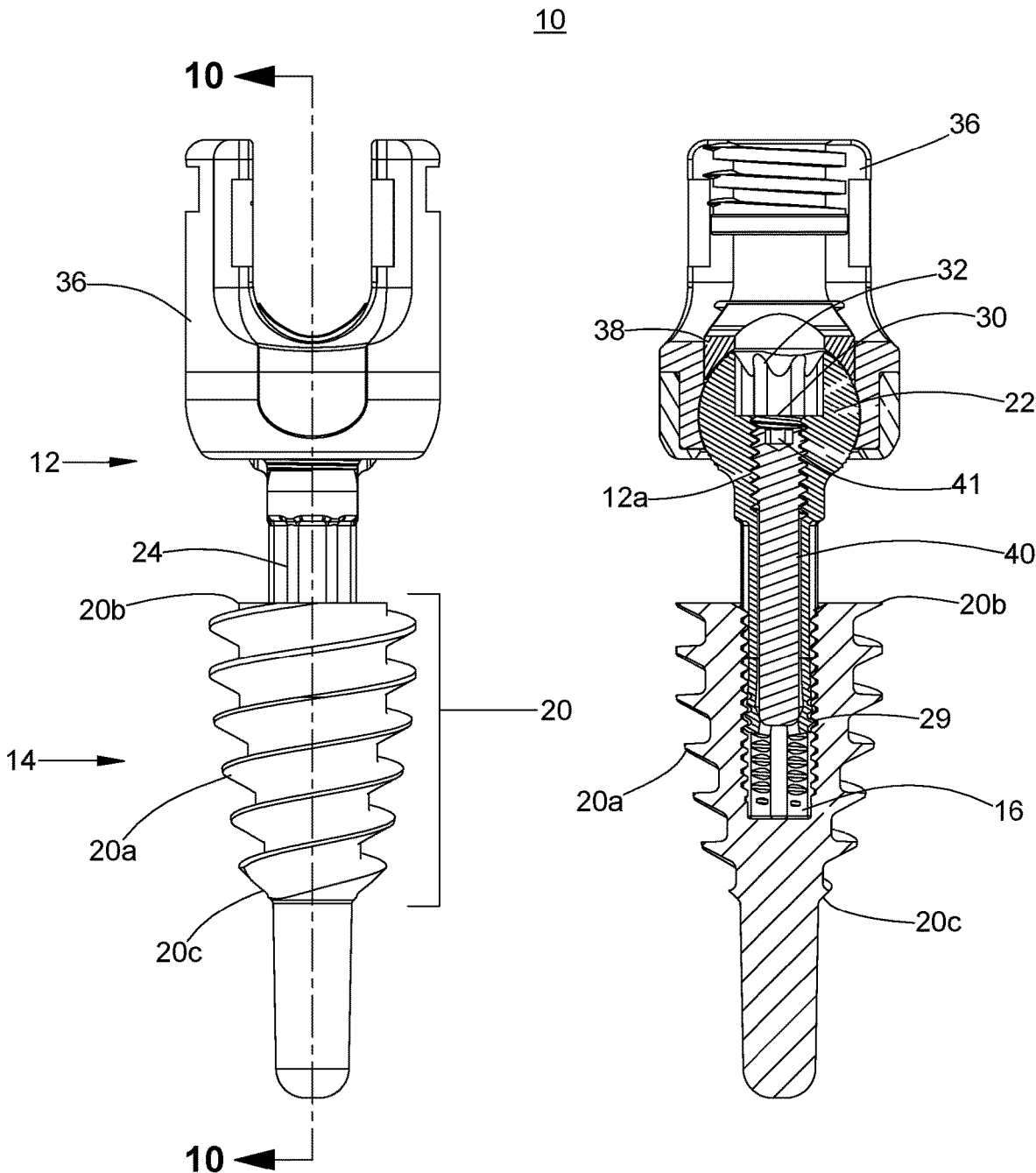
FIG. 9 is a side view of the modular screw of FIG. 1.
FIG. 10 is a side cross-sectional view of the modular screw of FIG. 9 cut along section line 10-10 of FIG. 9.

The screw shank 12 includes a polyaxial head 22, and a shaft 24 extending distally from the polyaxial head 22. The polyaxial head 22 may be a bulbous shape or any other shape that enables a range of motion of the screw shank 12 along different axes (i.e., rotational and pivotal movement). For example, the polyaxial head 22 may have a roughened outer surface to provide an enhanced gripping surface. The polyaxial head 22 may include a keyed opening 32 (FIG. 10) that extends into a second bore 30 (FIG. 10). The second bore 30 can be configured and dimensioned to receive the elongate screw 40.

The shaft 24 of the screw shank 12 includes a keyed outer surface 24a that extends from the polyaxial head 22 toward a distal end 12b of the screw shank 12. The keyed outer surface 24 can be configured and dimensioned to mate or engage at least a portion of an inner surface 18 (FIG. 2) of the post 14. For example, the keyed outer surface 24 may include longitudinal ridges 24b. The longitudinal ridges 24b and a multi-faceted inner surface 18 of the post 14 may include a complementary configuration. For example, the keyed outer surface 24a of the shaft 24 may include a star-shaped cross-section. However, any shape and any configuration of the keyed outer surface 24a may be utilized to form a complementary configuration with the inner surface 18 of the post 14.

Figure 8:
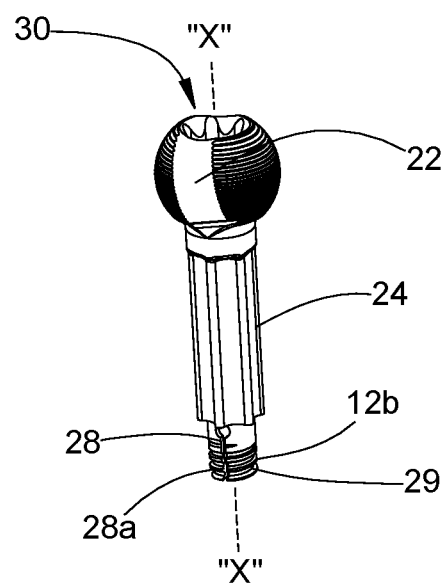
FIG. 8 is a perspective view of a screw shaft of the housing assembly of FIG. 7.

With reference to FIG. 8, the screw shank 12 includes a slit portion 28 defining slits 28a. The slit portion 28 is disposed near the distal end 12b of the screw shank 12. The slit portion 28 may include any number of slits 28a circumferentially arranged about a longitudinal axis "X-X" defined by the screw shank 12. The slits 28a enable radial expansion of the slit portion 28 when a force is applied thereto. The slit portion 28 also includes a gripping surface 29 (FIG. 10) configured to engage at least a portion of the inner surface 18 (FIG. 2) of the post 14. For example, a quarter of the slip portion 28 may include the griping surface 29. Alternatively, at least a half of the slip portion 28 may include the gripping surface 29. The gripping surface 29 is configured to grip, engage, or otherwise force fit the slit portion 28 with at least a portion of the inner surface 18 of the post 14 when the slit portion 28 is radially expanded. The gripping surface 29 may include, e.g., a shallow thread, a plurality of raised concentric rings, or, a roughened surface. The screw shank 12 includes a helical shallow thread. The helical shallow threads are configured and dimensioned to engage at least a portion of the inner surface 18 of the post 14.

Figure 4:
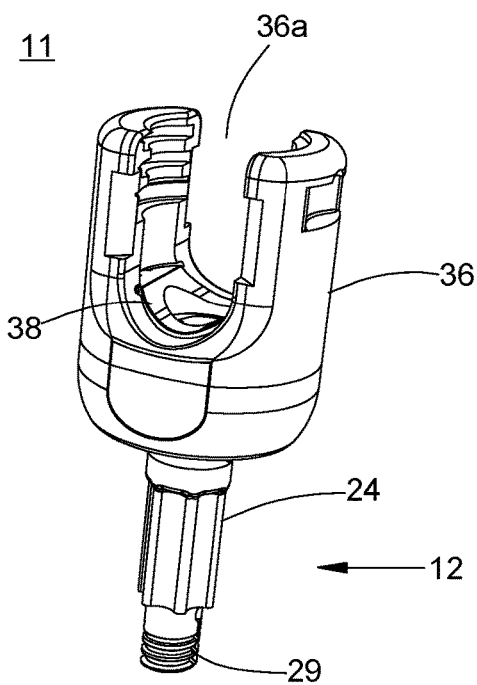
FIGS. 4-6 are perspective views of the housing assemblies illustrating various heights.
Figure 5:
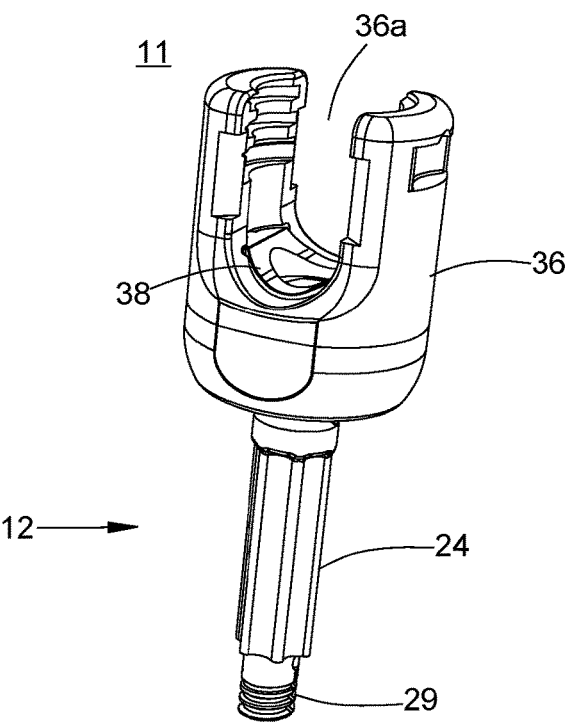
Figure 6:
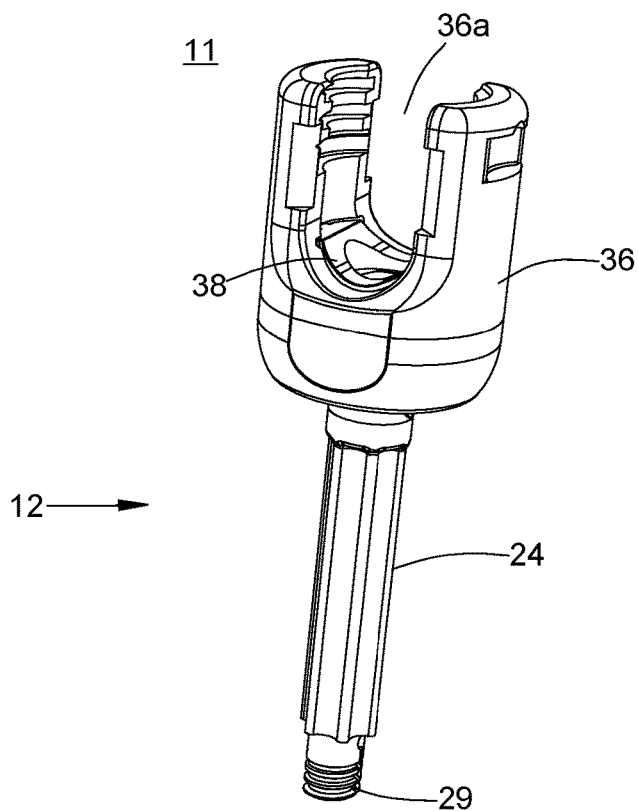

With reference back to FIG. 7, the head assembly 11 further includes the cap 42 configured to support the screw shank 12 and couple the screw shank 12 with the head 36. The screw shank 12 may be part of a head assembly as shown in FIG. 7 or may be part of a pre-assembled screw head system, as shown in FIGS. 4-6. A length of the screw shank 12 may be selectively adjusted. For example, a kit comprising a pre-assembled screw head system with a screw shank 12 of a first length (FIG. 4), a pre-assembled screw head system with a screw shank 12 of a second length (FIG.

5), and a pre-assembled screw head system with a screw shank 12 of a third length (FIG. 6) may be utilized during a surgery.

With brief reference back to FIGS. 1 and 2, the modular screw 10 further includes the post 14. The post 14 defines a first bore 16 having an opening 16*a* at a proximal end 14*a* of the post 14. The opening 16*a* is dimensioned to receive the screw shank 12. The post 14 includes the inner surface 18 defining the first bore 16. The inner surface 18 may be any configuration that is complementary to the configuration of the screw shank 12. As discussed hereinabove, the screw shank 12 has a star-shaped cross-section. At least a portion of the inner surface 18 includes a complementary star shape counter-relief configuration to receive the star-shaped screw shank 12. Although a star shape is illustrated, it is contemplated that other shapes as well as other keyed configurations may be used. In addition, at least a portion of the inner surface 18 of the post 14 includes a complementary threaded surface to engage or mate with the gripping surface 29 (FIG. 8) of the slit portion 28 of the screw shank 12 when the slit portion 28 is expanded radially outward. The inner surface 18 can also be configured and dimensioned to receive a driver (not shown). A force can be applied to the driver so that the post 14 can engage osseous tissue.

With reference now to FIGS. 9 and 10, the post 14 can includes a tapered portion 20. The tapered portion 20 can extend at least a quarter of a length of the post 14. The tapered portion 20 may extend at least a half of the length of the post 14. Alternatively, the tapered portion 20 may extend less than a quarter of the length of the post 14. The tapered portion 20 includes external threads 20*a*, such as helical threads, that can rotate clockwise or counter-clockwise around the tapered portion 20 of the post 14. The major diameter of the tapered portion 20 may be in the range of about 9 mm and about 13 mm. Alternatively, the major diameter of the tapered portion 20 may be in the range of about 10 and about 12 mm.

The major diameter may be tapered along the length of the post 14 at a ratio of major diameter at the proximal portion 20 *b* of the tapered portion 20 to a major diameter at the distal portion 20 *c* of the tapered portion 20 in the range of about 1 and about 2. Alternatively, the ratio may be in the range of about 1.4 and about 1.7. For example, an angle of the taper may vary from about 10 degrees to about 60 degrees. Furthermore, the angle may vary from about 18 degrees to about 56 degrees. The post 14 may include a diameter in the range of about 2 mm and 5 mm. Furthermore, the diameter of the post 14 may be in the range of about 3 mm and about 4 mm.

The external thread 20*a* is configured to engage osseous tissue, such as, e.g., a vertebra, or more particularly, a pedicle of a vertebra. When the post 14 is inserted into osseous tissue, such as a pedicle of a vertebra, the tapered portion 20 may fit within an isthmus of the pedicle.

In use, with reference to FIGS. 9 and 10, the clinician initially prepares the vertebrae (not shown). The clinician may form an insertion hole in, e.g., osseous tissue, by preparing the surface with a burr or other like instrument and then an awl to start the hole. The insertion hole may be formed into, e.g., a cortical shell of an upper portion of a pedicle. The tapered portion 20 of the post 14 may be inserted above and/or in, but not through, an isthmus of the pedicle, whereby the likelihood of breaching the pedicle and the need for navigation is reduced. Thereafter the post 14 may be inserted into the insertion hole. A driver (not shown) may be utilized to engage the keyed inner surface 18 of the post 14 to drive the tapered portion 20 of the post 14 into osseous tissue. Thereafter, the screw shank 12, optionally with a pre-loaded elongated screw 40, is inserted into the first bore 16 of the post 14. At this time, the screw shank 12 may be translated within the first bore 16 of the post 14 to a desired height. A driver (not shown) can then be inserted into the opening 41 of the elongate screw 40. A force can be applied to the driver so that the elongate screw 40 can engage a threaded inner surface of the second bore 30 of the screw shank 12. As discussed hereinabove, the elongate screw 40 imparts force to the griping surface 29 such that the gripping surface 29 of the screw shank 12 expands radially outward against at least a portion of the inner surface 18 of the post 14. In addition, an angle of the head 36 may be adjusted relative to the screw shank 12 by affixing or attaching the head assembly 11 to mechanical hardware. A spinal rod (not shown) or a band (not shown) may be inserted into the head 36 of the head assembly 11.

By selecting appropriately sized modular screws 10, the clinician can customize the rod construct to a patient's anatomy. In one non-limiting example, the clinician selects one or more modular screws 10 having a first height and one or more modular screws 10 having a second height. This allows the clinician to set the heights of the slots 36*a* of the heads 36 to more closely match the contour of the rod used in the spinal construct. Additionally, it also allows the clinician to adjust the angle and/or rotational orientation of the slots 36*a* to match the contour of the rod. Thus, one modular screw 10 may have a first slot 36*a* at height and a second modular screw 10 may have a slot 36*a* at a second height different from the first height.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A modular screw comprising:
   a post including a tapered portion extending along a portion of a length of the post, the post defining a first bore; and
   a head assembly adjustably coupled with the post, the head assembly including:
   a head defining a slot configured to receive a spinal rod therein;
   an elongate screw having external threads extending along a portion of a length of the elongate screw; and
   a screw shank defining a second bore defining internal threads configured to engage the external threads of the elongate screw when the elongate screw is received within the second bore of the screw shank, the screw shank including a shaft having a keyed outer surface including a longitudinal ridge and an engaging portion provided with a gripping surface, the engaging portion configured to expand radially outward when the elongate screw engages the engaging portion, wherein at least a portion of the screw shank is dimensioned to be selectively received in the first bore of the post.

2. The modular screw according to claim 1, wherein the engaging portion of the screw shank defines slits to facilitate radial expansion of the engaging portion.

3. The modular screw according to claim 1, wherein the engaging portion is axially spaced from the keyed outer surface along the shaft of the screw shank.

4. The modular screw according to claim 1, wherein at least a quarter of the engaging portion has the gripping surface.

5. The modular screw according to claim 1, wherein the gripping surface includes threads.

6. The modular screw according to claim 1, wherein the first bore of the post and the screw shank have complementary cross-sections.

7. The modular screw according to claim 1, wherein the screw shank includes a polyaxial head and the shaft extends distally from the polyaxial head.

8. The modular screw according to claim 7, wherein the polyaxial head of the screw shank is operatively coupled with the head for polyaxial movement relative to the head.

9. The modular screw according to claim 7, wherein the polyaxial head includes a bulbous shape.

10. The modular screw according to claim 1, wherein the tapered portion of the post extends at least a quarter of a length of the post.

11. The modular screw according to claim 1, wherein the tapered portion of the post extends at least a half of a length of the post.

12. The modular screw according to claim 1, wherein the tapered portion of the post includes external threads.

13. The modular screw according to claim 1, wherein a major diameter of the tapered portion of the post is in the range of about 10 mm and about 12 mm.

14. The modular screw according to claim 1, wherein the external threads of the elongate screw of the head assembly are spaced from the distal end of the elongate screw and extend at least a sixteenth of a length of the elongate screw.

15. The modular screw according to claim 14, wherein the external threads of the elongate screw of the head assembly extend at least an eighth of a length of the elongate screw.

16. The modular screw according to claim 15, wherein the external threads of the elongate screw of the head assembly extend at least a quarter of a length of the elongate screw.

17. The modular screw according to claim 1, wherein the elongate screw defines a cavity having a key feature for engagement with a driver to drive the elongate screw.

* * * * *